United States Patent [19]

List et al.

[11] 4,162,365

[45] Jul. 24, 1979

[54] LIQUID PHASE AIR OXIDATION PROCESS FOR MAKING PHTHALIC ACIDS

[75] Inventors: Ferdinand List; Helmut Alfs, both of Marl, Fed. Rep. of Germany

[73] Assignee: Chemische Werke Hüls Aktiengesellschaft, Marl, Fed. Rep. of Germany

[21] Appl. No.: 704,955

[22] Filed: Jul. 13, 1976

Related U.S. Application Data

[63] Continuation of Ser. No. 176,262, Aug. 30, 1971, abandoned, which is a continuation-in-part of Ser. No. 773,349, Nov. 4, 1968, abandoned.

[30] Foreign Application Priority Data

Nov. 11, 1967 [DE] Fed. Rep. of Germany ....... 1643827

[51] Int. Cl.² ............................................. C07C 51/33
[52] U.S. Cl. .................................................... 562/416
[58] Field of Search ..................... 260/524 R; 562/416

[56] References Cited

U.S. PATENT DOCUMENTS

| | | | |
|---|---|---|---|
| 3,139,452 | 6/1964 | Hays ................................ | 260/524 R |
| 3,354,202 | 11/1967 | Zimmerschiel et al. ........ | 260/524 R |

*Primary Examiner*—Paul J. Killos
*Attorney, Agent, or Firm*—Gilbert L. Wells

[57] ABSTRACT

An improvement in the liquid phase air oxidation process based upon a solvent system such as acetic acid and with a bromine activated heavy-metal catalyst system for preparing phthalic, isophthalic and terephthalic acids from their corresponding alkyl benzenes wherein the heavy metal is a soluble cobalt compound and sufficient excess of air is introduced so that the waste gas still contains an excess of oxygen.

18 Claims, No Drawings

LIQUID PHASE AIR OXIDATION PROCESS FOR MAKING PHTHALIC ACIDS

CROSS-REFERENCE TO RELATED APPLICATIONS

This is a continuation, of application Ser. No. 176,262, filed Aug. 30, 1971, now abandoned which in turn is a continuation-in-part of application Ser. No. 773,349, filed Nov. 4, 1968 and now abandoned.

Applicants claim priority under 35 U.S.C. 119 for an application having Ser. Nos. C 43 817 IVb/12 o and P 16 43 827.0, which was filed in the Patent Office of the Federal Republic of Germany on Nov. 11, 1967.

BACKGROUND OF THE INVENTION

The field of the invention is aromatic carboxylic acids, and particularly the method of preparing phthalic, isophthalic and terephthalic acids by the liquid phase air oxidation of the corresponding alkyl benzenes dissolved in lower carboxylic acids and in the presence of a bromine activated heavy metal catalyst system.

The state of the prior art may be ascertained by reference to the Kirk-Othmer "Encyclopedia of Chemical Technology", 2nd Edition, Vol. 15, pages 444–487 under the section "Phthalic Acids". Kirk-Othmer points out, at page 451, that one of the four fundamentally different reaction processes for preparing phthalic acids is a liquid phase air oxidation process based upon a solvent system such as acetic acid and with a bromine activated heavy metal catalyst system. This process is based upon the oxidation of mixed xylenes to mixed phthalic, isophthalic and terephthalic acids. Phthalic, isophthalic and terephthalic acids are also called respectively, ortho-, meta- and parabenzene dicarboxylic acids.

The state of the prior art is also shown by U.S. Pat. Nos. 2,245,528 of Loder; 2,276,774 of Henke; 2,415,800 and 2,833,816; West German Printed Specifications (DAS) Nos. 1,004,159; 1,081,445; 1,130,447; 1,168,867; 1,210,790; and 1,235,887; East German Pat. No. 10,918; and the reference Chem. Ing. Techn. 34,51 (1962).

Ever since the disclosure of the U.S. patent of Loder, it has been generally known that toluic and phthalic acids can be obtained by the air oxidation of xylenes dissolved in lower carboxylic acids when certain heavy metal compounds are used as catalysts, preferably, among others, compounds of vanadium, cerium, cobalt and manganese.

The U.S. patent of Henke suggested performing the oxidation also in the presence of barium or lead compounds. Optimum results were first obtained with the addition of barium and lead bromide as suggested by Henke and others if, in accordance with U.S. Pat. No. 2,415,800 and East German Pat. No. 10,918, hydrogen bromide was used to promote continuous oxidation to the final end product.

Ever since these early teachings, the air oxidation process has been repeatedly described and modified. German Printed Specifications Nos. 1,081,445; 1,130,447; as well as 1,210,790, and U.S. Pat. No. 2,833,816, and also, for example, Chem. Ing. Techn. 34,51 (1962), show that catalytic systems which contain manganese are especially effective. Thus, in German Printed Specification No. 1,004,159, Example 3, it is clearly stated that manganese produces a much higher yield of a better product than is obtained with cobalt.

It has been observed that phthalic acids which are formed by the known air oxidation processes, and especially the terephthalic acid, are extremely finely granular. This is especially true of those terephthalic acids which are produced from p-xylene. Thus, German Printed Specification No. 1,235,887 shows in its examples that, depending on the specific method of preparation, there are obtained average terephthalic acid particle sizes of only 0.5 to $2.0\mu$.

These fine suspensions settle very slowly and the separation and processing of these suspensions presents great difficulty, especially during large quantity production. Such a finely suspended acid cannot be separated in the standard centrifuges or decanters. A finely grained acid can only be isolated by using standard filtration methods with the use of suction filters or filter presses. According to the German Printed Specification No. 1,235,887, the separation is performed in a rotary filter.

There are also serious difficulties with the filtration methods because the very small particle sizes form a filter cake which is practically impermeable. The grains are deposited in the pores of the filter medium and this greatly retards the filtration and necessitates the use of unusually large filtration surfaces. It is also to be considered that the diminution of filter output by the fine particles is caused not only by the obstruction of the pores in the filter medium, but also in a large measure by the absorption of the mother liquor by the surface forces of the filter material. These surface forces become very prominent because of the rapid increase of surface area which results from diminishing particle size. These surface forces impose a limit on the dewatering and washing of the filter cake. In the process disclosed in German Printed Specification No. 1,235,887, the separated phthalic acid has a residual moisture content greater than 50%, which frequently renders the filtration product thixotropic and makes the washing and drying very expensive. The above-identified problem has been pointed out in German Printed Specification No. 1,047,192 and in this disclosure an effort has been made to solve the problem for the production of phthalic acid by oxidation with nitric acid.

For those phthalic acids which are obtained by the methods of Loder, Henke and others, the problem still remains unsolved.

SUMMARY OF THE INVENTION

It is therefore an object of the present invention to modify the known phthalic acid production processes so that larger phthalic acid particles are formed which can be separated in the standard centrifuges and washed.

In the present invention this problem is solved by using as a heavy metal compound a soluble cobalt compound and a sufficient excess of air so that the waste gas still contains an excess of oxygen. The phthalic acids produced can be any of the ortho-, meta- and para-benzene dicarboxylic acids or mixtures thereof, but the present invention is particularly concerned with terephthalic acid.

According to the present invention, air oxidation is understood to include every process wherein an oxygen containing gas is used. The cheapest and most convenient gas used is air, but obviously, with due consideration to explosion danger, it is also possible to use air that has been enriched with oxygen or nitrogen, or to use oxygen which contains an inert gas.

DESCRIPTION OF THE PREFERRED EMBODIMENTS

The present invention is carried out by the excess air oxidation of ortho-, meta- and para-xylenes, corresponding to the phthalic acids to be produced, dissolved in a lower carboxylic acid in the presence of a bromine activated cobalt catalyst system.

The lower carboxylic acids used as solvents are generally aliphatic monocarboxylic acids having 1–8 carbon atoms, especially 2 to 4 carbon atoms, such as acetic acid, propionic acid, butyric acid, trimethyl acetic acid, isobutyric acid and methoxy-butyric acid. The preferred solvent is acetic acid.

As initial substances for the oxidation, the three corresponding ortho-, meta- and para-xylenes are preferred, but it is also possible to use dialkyl benzenes in which the side chains are longer and/or substituted, e.g. diethyl-benzene, diisopropyl-benzene, cymene or those in which the side chains are halogen substituted, such as xylene chloride, xylene bromide, etc. Also intermediate oxidation products such as toluic aldehydes, toluic acids, toluic alcohols, phthal aldehyde acids, phthal dialdehydes, etc. are also useful. The concentration of the alkyl benzenes in the lower carboxylic acids may vary from 1 weight % to 50 weight %, with a preferred concentration range of 5 weight % to 25 weight %.

The heavy metal compounds used in the invention are exclusively cobalt compounds which are preferably soluble in lower carboxylic acids, in mixtures of lower carboxylic acids with water or in mixtures with hydrocarbons, for example, cobalt compounds of inorganic and organic acids, cobalt soligens, etc. The preferred compound is cobalt acetate and the concentration range is from 1 gram to 10 grams, and preferably 2 to 6 grams per liter of reaction solution.

In addition to cobalt acetate, the following specific cobalt compounds are useful:
cobalt chloride
cobalt permanganate
cobalt nitrate
cobalt-III-potassium nitrite
cobalt-III-sodium nitrite
cobalt toluate
cobalt propionate
cobalt butyrate
cobalt isobutyrate
cobalt naphthenate
cobalt octoate The bromine compounds useful in the catalyst system are, for example, inorganic bromine compounds such as barium bromide $BaBr_2$, lead bromide $PbBr_2$, cobalt bromide $CoBr_2$, hydrogen bromide HBr, ammonium bromide $NH_4Br$, potassium bromide KBr, etc.; organic bromine compounds such as ethyl bromide, ethylene bromide, bromoform, xylylbromide, xylylene bromide, etc. The bromine compounds preferably used are barium bromide $BaBr_2$ or potassium bromide KBr. The bromine compound is used in such a concentration that the organically or inorganically combined bromine amounts to about 0.5 to 10.0 grams, and preferably 1.5 to 4.0 grams per liter of reaction solution.

Illustrations of particular combinations of cobalt bromine catalyst systems are: cobalt acetate and potassium bromide KBr, cobalt acetate and ammonium bromide, cobalt acetate and lead bromide, cobalt acetate and barium bromide, cobalt naphthenate and ethylene bromide, cobalt isobutyrate and bromoform, cobalt chloride and monobromoacetic acid.

As examples of the overall combination of alkyl benzene dissolved in a lower carboxylic acid and having a cobalt bromine catalytic system, the following combinations are given: paraxylene dissolved in acetic acid with cobalt acetate and KBr; para-cymene dissolved in propionic acid with cobalt acetate and monobromoacetic acid; para-diethyl benzene in butyric acid with cobalt nitrite and ethylene bromide; para-toluic acid in acetic acid with cobalt acetate and $BaBr_2$; phthalaldehyde acid in isobutyric acid with cobalt naphthenate and lead bromide.

According to the invention, a sufficient excess of air is used in the oxidation so that the reaction will contain at all times a large excess of oxygen. Specifically, an excess of oxygen is present from the start of the oxidation. This is accomplished when, after thorough agitation of the reaction mixture, the waste gas still contains at least 2% volume of excess oxygen. The excess oxygen is preferably 2–4%. The upper limit of excess oxygen can be greater than 4%, but generally there is no advantage to increasing the volume of oxygen beyond 4%, since with the increase in oxygen there is a greater danger of explosions.

The oxygen can be readily determined during the oxidation, as for example, by means of a magnetic measuring device, and regulation of the oxygen content can be completely automatic by increasing or diminishing the amount of oxygen input.

The reaction can be performed in any number of different vessels that will permit vigorous stirring, as for example, a closed container equipped with an agitator in the form of a radial rotary stirrer through whose arms the oxygen is introduced. The container must also be equipped with a product removal device, for example, in the form of an automatically actuated collapsible or conical valve and a cooling system.

When the process is performed continuously, during long periods of time, the removal of frequently occurring and very hard vitreous deposits becomes a major problem. For this purpose the apparatus described in German Printed Specification No. 1,168,887 has been found especially suitable. The oxidation of p-xylene is performed therein in a reaction tower with peripheral movement. The terephthalic acid formed is insoluble in the reaction mixture and is continuously thrown out from the tower. The amount that is thrown out is measured in such a manner that the height of the material in the tower is maintained constant. The terephthalic acid suspension removed is delivered to a vessel with a stirrer in which it is cooled to room temperature, where a phase separation commences. The mother liquor, which in addition to the solvent also contains intermediate oxidation products, hydrocarbon starting material and contact salt, is returned to the oxidation tower. At the same time additional p-xylene is added to compensate for that converted into terephthalic acid.

Contrary to the instructions disclosed by the patent literature, the oxidation of the present invention is performed in the complete absence of manganese oxidation catalysts which have generally been considered as being especially effective, but instead is performed in the presence of only cobalt and bromine ions.

It is particularly surprising that the manganese salts, although functioning as oxidation catalysts, are apparently effective only for the formation of intermediate oxidation products which accumulate in the mother liquor. This continues to such an extent that with the addition of only manganese ions besides the bromine ions, in spite of good oxygen absorption, p-xylene, for example, produces hardly any terephthalic acid. Instead there is formed a dark brown oily reaction mixture which contains only traces of terephthalic acid. In this acetic acid reaction solution there are produced, besides small amounts of non-reacted hydrocarbons, the following and other intermediate oxidation products in high concentrations (up to 15%): p-toluic acid, p-methoxybenzoic acid, terephthalaldehyde acid and benzoic acid.

The reaction solution also contains colored by-products which are formed by secondary reactions from labile intermediate reaction products.

If this reaction solution is diluted with water in the ratio of 1:5, there is formed first a milky-white emulsion, from which the intermediate oxidation products precipitate as white and partly as viscid flakes.

Also with the prior art addition of a cobalt and manganese ion mixture to the bromine ions, the proportion of the intermediate oxidation products in the mother liquor, as shown by the water test, is relatively high (>5%). Although terephthalic acid precipitates, it is extremely fine grained and contains colloidal particles throughout. The result is that this acid can be separated from the reaction solution only by filtration whereby the very fine viscid particles will form a dense and difficultly permeable filter cake.

In the presence of the excess of oxygen of the present invention, the above-mentioned labile intermediate oxidation products which react further with the formation of colored by-products, are further oxidized quickly to stable end-products. Hence, in accordance with the present invention, only cobalt salts are used in conjunction with an excess of oxygen.

Since the proportion of intermediate oxidation products in the reaction mixture has a decisive effect on the phthalic acid that is formed, and especially on the granules, but also on the color etc., the oxidation is performed in such a manner that the level of intermediate reaction products is kept as low as possible. This requirement is sufficiently fulfilled if the concentration of the intermediate oxidation products is kept below 30 g/l of reaction solution.

The concentration of the intermediate reaction products is easily determined if, as described above, the reaction solution is diluted with water in the proportion of 1:5. In this manner there is first formed an emulsion, from which the substances precipitate so that they can be separated.

Generally it is not necessary to make such a determination since it has been shown that a reaction solution which contains more of the intermediate oxidation products than can be permitted is dark brown in color and opaque, whereas a reaction solution which yields products whose qualities are commensurate with those of this invention is clearly transparent and of the color of raspberry beer.

It is therefore not difficult to keep the intermediate oxidation products down to the required level because it is only necessary to control the appearance of the reaction mixture. If an undesired increase of intermediate product content is notices, then fresh hydrocarbon is added in the meantime. If sufficient gas velocity is available (maximum velocity 20 cm/sec., relative to the free cross section), then the introduction of oxygen is increased. Sometimes the reaction speed is increased by the addition of fresh catalyst, or the formation of intermediate oxidation products is sometimes stopped by increasing the temperature 10° to 20°. The above-mentioned measures are applied separately or together until the level of intermediate products in the mother liquor has receded to a permissible value.

In this manner process conditions are corrected in a simple manner, for example, in cases where such conditions have resulted from undesired temperature drops or other nonforeseeable influences on the catalytic process.

By use of a continuous process, the condition of the reaction solution is observed continuously if desired by a color or turbidity test of the dicarboxylic acid free reaction mixture and is regulated with the help of the above-mentioned measures.

For maintaining favorable conditions with reference to the intermediate products, even during a continuous oxidation process, the process is carried out as follows:

p-Xylene, which together with the acetic acid solvent has been brought into the presence of the cobalt-bromine catalyst, is first oxidized discontinuously until no more oxygen is absorbed. It is not until then that additional p-xylene is added in such amounts that during the ensuing continuous process the proportion of intermediate oxidation products in the mother liquor does not exceed the value of 30 g/liter.

As discussed above, the oxidation of the xylenes in the presence of heavy metal compounds and bromine compounds has been known in the art. In accordance with the present invention, this conventional xylene oxidation is preferably conducted with high theoretical and space-time yields at a temperature of from 160° to 190° C. Above 200° C., the corrosion problem becomes much more serious, and the solvent system, for example, acetic acid, becomes extensively dissolved by oxidation. Moreover, in order to achieve the advantageous results of the invention, it is necessary (1) to employ only cobalt in addition to bromine in the reaction, (2) to keep an excess of oxygen present in the system from the beginning of the oxidation, and (3) to keep the level of intermediate product in the reaction solution as low as possible. Using these reaction conditions, the thus-obtained phthalic acids have an exceedingly high quality and are, furthermore, of a granular crystalline structure and thus can be readily separated from the oxidation mixture.

The pressure range employed in connection with the process of this invention is from about 2 to 30 atmospheres, with the preferred range being 5 to 15 atmospheres. The contact time between the reactants and the oxygen-containing gas is from about 10 to 300 minutes, preferably 30 to 200 minutes. The oxygen-containing gas, such as air, is added to the reactants at a rate sufficient for achieving the novel excess of oxygen in the waste gas, the rate being dependent, of course, on the conditions of the apparatus and process.

Under the defined conditions there is formed in the reaction mixture a very clean white dicarboxylic acid with coarse granules (80% > 100$\mu$). This acid is continuously separated from the reaction mixture and simultaneously washed in a simple manner in a completely jacketed centrifuge. By this method all impurities such as intermediate oxidation products and contact salts are removed from the mother liquor and the acetic acid washing liquid from the terephthalic acid so that the latter can be subjected immediately to further processing. The residual moisture in the terephthalic acid that comes from the centrifuge amounts to only 5 to 10%.

With this degree of dryness the acid is dispersible so that its subsequent treatment, including first the further drying, is very simple. The mother liquor from the centrifuge contains only traces of terephthalic acid (<1%). The mother liquor is clearly transparent, red in color and upon dilution with water does not become turbid. It is returned to the oxidation apparatus together with the acetic acid washing liquid. In the defined process there is not noticeable deterioration of the terephthalic acid quality even after 300 hours of continuous operation.

A special characteristic of the acid obtained under the defined conditions is, among others, also its good color quality. This is shown by a comparison of different terephthalic acid patterns whereby a comparison is made of the optical transparencies of different terephthalic acid patterns of solutions of 4% by weight of acid in ammonia, using a layer of solution 4 cm thick and a light source of 380μ. (The optical transparency is expressed as the logarithm of the ratio: Incident light/Transmitted light, so that for 100% transmission, the logarithm would be zero).

The following values have been measured:
Oxidation according to this invention—0.07
Oxidation under the prior art—5.7

Without further elaboration, it is believed that one skilled in the art can, using the preceding description, utilize the present invention to its fullest extent. The following preferred specific embodiments are, therefore, to be construed as merely illustrative, and not limitative of the remainder of the specification and claims in any way whatsoever.

EXAMPLE 1

To prove the foregoing, a few discontinuous oxidation processes were performed in a 5 liter titanium column as described in German Printed Specification No. 1,168,887. This tower is equipped with lateral circulation, with high pressure steam heating, an air introducing connection, an air purifier, a safety valve and an oxygen measuring device in the waste gas conduit. In each case the waste gas contains a certain oxygen excess amounting to 2 to 4% by volume.

If instead of the circulation apparatus, a closed container is used equipped with a stirrer having hollow arms through which air is introduced, an automatically regulated conical discharge valve and a cooling circulation for conveying away the heat, then entirely similar results are obtained.

Similar results will also be obtained if instead of p-xylene, toluic acid or other intermediate oxidation products are used as the starting substance.

In Table I are illustrated the conditions and results of carrying out the present invention as compared to the prior art methods. The use of cobalt acetate-KBr catalyst is representative of the present invention. The manganese acetate-KBr and cobalt acetate-manganese acetate-KBr catalysts are representative of the prior art.

TABLE I

| Contents | | Conditions | | | Intermediate product concentration | Terphthalic acid | | | Separation of the terphthalic acid | | | Mother Liquor | |
| --- | --- | --- | --- | --- | --- | --- | --- | --- | --- | --- | --- | --- | --- |
| Hydro-Carbon/Acetic acid | Catalyst | T °C. | P atm | Time Mins. | G/kg mother liquor | % | g | acid No. | % | Color granule μ | Filtration | Centrifuging | Residual | Color | Color Water-dilution 1:5 |
| 600 g p-xylene 2500 g HAc | 20 g CoAc₂ 10 g KBr | 180 | 15 | 60 | 20 | 2 | 840 | 673 | 99.8 | White 80% >100 μ | Unnecessary | yes | 5-10% | Light rose red | Light rose red |
| 600 g p-xylene 2500 g HAc | 20 g MnAc₂ 10g KBr | 180 | 15 | 60 | 220 | 22 | 64 | 641 | 95 | yellow 1-10 μ | yes | Impossible | >50% | Dark Brown | Milky White flocculation |
| 600 g p-xylene 2 g HAc | 10 g CoAc₂ 10 g MnAc₂ 10 g KBr | 180 | 15 | 60 | 60 | 6 | 600 | 660 | 98 | yellow 1-30 μ | yes | Impossible | >50% | Brown | Milky white flocculation |

EXAMPLE 2

500 g of o-xylene are dissolved in 2500 g of acetic acid and are oxidized with air in the presence of 20 g of cobalt acetate and 10 g of potassium bromide in the apparatus described in Example 1 while the following conditions are maintained:

| | |
| --- | --- |
| Temperature | 160° C. |
| Pressure | 10 atm. |
| Air load | 1.2 m² per hour |
| Running time | 2 hours |
| O₂ in waste gas | 3 to 4% |

The reaction mixture is then discharged and is cooled to room temperature. The precipitated o-phthalic acid is separated from the mother liquor in a full jacketed centrifuge and is washed with acetic acid. The centrifuged acid has a residual moisture content of 10% and a grain size of 100 to 150μ. After drying, 760 g of o-phthalic acid with an acid number of 674 (=100%) is obtained. The color of the product is snow white. In the rose red clear transparent mother liquor, besides small amounts (2%) of intermediate products, there are also 68 g of p-phthalic acid in solution which can be obtained in a simple manner by distillation of the solvent. The total yield amounts to 94% of the theoretical, based on the original hydrocarbon. A distillative processing of the mother liquor is not necessary if the mother liquor is replenished with fresh hydrocarbon and is again subjected to oxidation.

EXAMPLE 3

Table II illustrates the conditions and results of the oxidation of m-xylene performed in the same manner as in Example 1.

TABLE II

| Contents | Conditions | | | | | Isophthalic acid (IPA) | | | | Separation of IPA | | | Mother Liquor | | |
| --- | --- | --- | --- | --- | --- | --- | --- | --- | --- | --- | --- | --- | --- | --- | --- |
| Hydrocarbonl HAc | Catalyst | T °C. | p atm | time min. | g | Acid No. | % IPA | Color | Grain μ | Filtration | Centrifuging | Residual moisture | Color | Color $H_2O$ diluted 1:5 | Intermediate product conc. g/kg |
| 600 g m-xylene 2500 g HAc | 20 g $CoAc_2$ 12 g $BaBr_2$ | 180 | 15 | 60 | 828 | 670 | 99.6 | White | 70 100 μ | — | yes | 12% | Light Rose Clear | Light Rose Clear | 22 |

The preceding examples can be repeated with similar success by substituting the generally and specifically described reactants and operating conditions of this invention for those used in the preceding examples.

Again, it is emphasized that an essential feature of this invention is to keep an excess of oxygen present at all times, particularly at the beginning of the oxidation reaction. Otherwise, condensation products of the carbonyl compounds formed as intermediates are immediately produced. These secondary products which are, in part, strongly colored, are then extraordinarily stable against any further oxidative attack. They can be converted into the desired phthalic acids only by means of a post-oxidation under very strict temperature conditions, of around 250° C., which are clearly unfavorable as such a temperature condition brings about insurmountable corrosion problems and degradation of the solvent system.

In order to achieve the advantageous results of this invention, it is necessary and desirable to use a catalytic amount of said bromine-activated cobalt compound. The amounts found to be useful in connection with this invention range from 0.5 to 5 g of cobalt per liter of reaction solution, preferably from 1 to 2.5 g.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

We claim:

1. In a process for the liquid phase oxidation of a dialkyl benzene dissolved in a lower carboxylic acid at a concentration of 5 to 25 weight % with a molecular oxygen-containing gas in the presence of a bromine-activated heavy metal compound catalyst to give phthalic, isophthalic and terephthalic acids, the improvement which comprises carrying out the oxidation at a temperature of 160° to 190° C. in the presence of said catalyst consisting essentially of a catalytic amount of a bromine-activated cobalt compound ranging from 0.5 to 5 grams of cobalt per liter of reaction solution and introducing a sufficient amount of said oxygen-containing gas into said liquid phase such that the reaction will contain a large excess of oxygen at all times and the waste gas produced contains an excess amount of oxygen, forming coarse granules of dicarboxylic acid where 80% of said particles are greater than 100 microns and continuously separating said granules in a centrifuge.

2. The process of claim 1, wherein the concentration of intermediate oxidation products is maintained below 30 grams per liter of reaction solution.

3. The process of claim 1, wherein said cobalt compound is cobalt acetate.

4. The process of claim 1, wherein said bromine-activated heavy metal compound is potassium bromide and cobalt acetate.

5. The process of claim 4, wherein said lower carboxylic acid is acetic acid.

6. The process of claim 5, wherein said dialkyl benzene is selected from the group consisting of o-xylene, m-xylene, p-xylene and mixtures thereof.

7. The process of claim 6, wherein said dialkyl benzene is p-xylene and the product is terephthalic acid.

8. The process of claim 6, wherein the concentration of said potassium bromide is about 0.5 to 10 grams per liter of reaction solution and the concentration of said cobalt acetate is about 1.0 to 10 grams per liter of reaction solution.

9. The process of claim 8, wherein the concentration of said potassium bromide is about 1.5 to 4 grams per liter of reaction solution and the concentration of said cobalt acetate is about 2 to 6 grams per liter of reaction solution.

10. The process of claim 1, wherein the lower carboxylic acid solvent is acetic acid.

11. A process for the liquid phase oxidation of a dialkyl benzene dissolved in a lower carboxylic acid at a concentration of 5 to 25 weight percent to give phthalic, isophthalic and terephthalic acids which comprises introducing an excess amount of a molecular oxygen-containing gas into said liquid phase in the presence of a catalyst consisting essentially of a catalytic amount of a bromine-activated cobalt-containing compound ranging from 0.5 to 5 grams of cobalt per liter of reaction solution and conducting the oxidation at a temperature of 160° to 190° C., the amount of oxygen-containing gas being present in large excess at all times during the oxidation such that the waste gas produced contains at least 2% by volume of oxygen, forming coarse granules of dicarboxylic acid where 80% of said granules are greater than 100 microns and continuously separating said granules in a centrifuge.

12. The process of claim 11, wherein the excess of oxygen in the waste gas is from 2 to 4% by volume.

13. The process of claim 12, wherein the concentration of intermediate oxidation products is maintained below 30 grams per liter of reaction solution.

14. The process of claim 13, wherein said bromine-activated cobalt-containing compound is potassium bromide and cobalt acetate and said lower carboxylic acid solvent is acetic acid.

15. The process of claim 11, wherein said oxygen-containing gas is air.

16. The process of claim 11, wherein said oxygen-containing gas is air enriched with oxygen.

17. The process of claim 11, wherein said oxygen-containing gas is air enriched with oxygen.

18. The process of claim 11, wherein said oxygen-containing gas is air enriched with nitrogen.

* * * * *